United States Patent [19]

Ochi et al.

[11] Patent Number: 4,950,605
[45] Date of Patent: Aug. 21, 1990

[54] FR-900493 SUBSTANCE, A PROCESS FOR ITS PRODUCTION AND A PHARMACEUTICAL COMPOSITION CONTAINING THE SAME

[75] Inventors: Kozo Ochi; Masami Ezaki; Morita Iwami, all of Tsukuba; Tadaaki Komori, Takatsuki; Masanobu Kohsaka, Tsukuba, all of Japan

[73] Assignee: Fujisawa Pharmaceutical Co., Ltd., Osaka, Japan

[21] Appl. No.: 319,042

[22] Filed: Mar. 6, 1989

[30] Foreign Application Priority Data

Mar. 18, 1988 [GB] United Kingdom ............... 8806429

[51] Int. Cl.$^5$ .................... C12N 1/20; C12N 1/02; C12R 1/085; A61K 35/00
[52] U.S. Cl. ................... 435/252.5; 424/116; 435/834; 435/261; 435/105
[58] Field of Search .......... 435/105, 252.5, 834, 435/261; 424/116

[56] References Cited

U.S. PATENT DOCUMENTS 4,458,078  7/1984  Kitaura et al. ............ 548/227
4,666,890  5/1987  Kitaura et al. ............ 514/18

*Primary Examiner*—Ronald W. Griffin
*Assistant Examiner*—Pamela S. Webber
*Attorney, Agent, or Firm*—Oblon, Spivak, McClelland, Maier & Neustadt

[57] ABSTRACT

FR-900493 is a compound of molecular formula $C_{20}H_{33}N_5O_{11}$ which may be recovered from Bacillus cultures, possesses antimicrobial activity, and may be used for the treatment and prevention of infectious diseases in humans and animals.

6 Claims, 3 Drawing Sheets

SPECTRUM OF INFRARED ABSORPTION
OF FR-900493 IN Kbr

SPECTRUM OF ¹H NUCLEAR MAGNETIC RESONANCE OF FR-900493 IN D₂O

SPECTRUM OF $^{13}C$ NUCLEAR MAGNETIC RESONANCE OF FR-900493 IN $D_2O$

FR-900493 SUBSTANCE, A PROCESS FOR ITS PRODUCTION AND A PHARMACEUTICAL COMPOSITION CONTAINING THE SAME

This invention relates to a novel compound having pharmacological activities, hereinafter entitled FR-900493 substance, to a process for its production and to a pharmaceutical composition containing the same.

More particularly, it relates to a novel compound, FR-900493 substance which has pharmacological activities such as antimicrobial activity, or the like, to a process for its production and to a pharmaceutical composition containing the same.

Accordingly, one object of this invention is to provide a novel compound, FR-900493 substance which is useful for treatment and prevention of infectious diseases, and the like.

Another object of this invention is to provide a process for production of the FR-900493 substance by fermentation of a FR-900493 substance-producing strain belonging to the genus Bacillus in a nutrient medium.

A further object of this invention is to provide a pharmaceutical composition containing, as an active ingredient, the FR-900493 substance.

Still further object of this invention is to provide a use of the FR-900493 substance for the treatment and prevention of infectious diseases, and the like.

The FR-900493 substance of this invention can be produced by fermentation of a FR-900493 substance-producing strain belonging to the genus Bacillus such as *Bacillus cereus* No. 2045 in a nutrient medium.

Particulars of microorganism used for the production of the FR-900493 substance will be explained in the following.

THE MICROORGANISM

The microorganism which can be used for the production of the FR-900493 substance is a FR-900493 substance-producing strain belonging to the genus Bacillus, among which *Bacillus cereus* No. 2045 has been newly isolated from a soil sample obtained from Amami-Oshima, Kagoshima Prefecture, Japan.

A lyophilized sample of the newly isolated *Bacillus cereus* No. 2045 has been deposited with an International depository authority on Budapest treaty, the Fermentation Research Institute, Agency of Industrial Science and Technology (1-3, Higashi 1-chome, Tsukuba-shi, Ibaraki-ken 305, JAPAN under the accession number of FERM BP-1791 (deposited date: Mar. 10, 1988).

It is to be understood that the production of the novel FR-900493 substance is not limited to the use of the particular organism described herein, which is given for the illustrative purpose only. This invention also includes the use of any mutants which are capable of producing the FR-900493 substance including natural mutants as well as artificial mutants which can be produced from the described organism by conventional means such as irradiation of X-rays, ultra-violet radiation, treatment with N-methyl-N'-nitro-N-nitrosoguanidine, 2-aminopurine, and the like.

The *Bacillus cereus* No. 2045 has the following morphological, and physiological characteristics.

[1] Morphological Characteristics:
The methods described in Bergey's Manual of Determinative Bacteriology (8th edition) were employed principally for this taxonomic study.

Morphological observations were carried out by the optical and electron microscopes with cells cultured on bouillon broth and agar at 30° C. for 12 hours. Results were shown in Table 1.

TABLE 1

| Morphological characteristics of strain No. 2045 | |
| --- | --- |
| Gram stain | Positive |
| Color of colony | Wax-colored |
| Cell shape | Rod |
| Cell size | $0.9 - 1.1 \times 3 - 5 \ \mu m$ |
| Spore | Positive, endospore |
| Spore position | Central to terminal |
| Motility | Positive |
| Flagella | Lateral |

[2] Physiological Characteristics:
Physiological characteristics of strain No. 2045 were summarized in Table 2.

TABLE 2

| Physiological characteristics of strain No. 2045 | |
| --- | --- |
| Conditions | Characteristics |
| Growth temperature | 18° C.–42° C. |
| Catalase | positive |
| TSI | Negative |
| Indol | Negative |
| $H_2S$ production | Negative |
| Urease activity | Negative |
| Gelatin liquefaction | Positive |
| Nitrate reduction | Positive |
| NaCl tolerance | 3%–5% |
| Starch hydrolysis | Weakly positive |
| Milk peptonization | positive |
| Milk coagulation | Negative |
| VP | Positive |
| Lysozyme sensitivity | Resistant |
| Growth in anaerobic agar | Positive |
| Simmons citrate | Positive |
| Growth on pH 5.7 agar | Positive |
| Hemolysis (horse blood agar) | Positive |
| G + C content (mole %) | 34–35 mole % |
| Virulency (mouse) | Positive |
| Acid from sugar | |
| D-glucose | Positive |
| L-arabinose | Negative |
| D-xylose | Negative |
| Mannitol | Negative |

According to Bergey's Manual of Determinative Bacteriology (8th edition), strain No. 2045 was considered to belong to genus Bacillus Cohn 1872 from those characteristics described above. After comparing the characteristics of Bacillus species described in Bergey's Manual of Determinative Bacteriology (8th edition), *Bacillus cereus* Frankland and Frankland 1887 was selected for further detailed comparison. So that, strain No. 2045 was compared with *Bacillus cereus*. No significant difference was observed between the two cultures and the properties of strain No. 2045 showed good agreement with *Bacillus cereus*. Strain No. 2045, therefore, was identified as *Bacillus cereus*.

PRODUCTION OF FR-900493 SUBSTANCE

The novel FR-900493 substance of this invention can be produced by culturing a FR-900493 substance-producing strain belonging to the genus Bacillus (e.g. *Bacillus cereus* No. 2045 FERM BP-1791) in a nutrient medium.

In general, the FR-900493 substance can be produced by culturing the FR-900493 substance-producing strain in an aqueous nutrient medium containing sources of assimilable carbon and nitrogen, preferably under aerobic conditions (e.g. shaking culture, submerged culture, etc.).

The preferred sources of carbon in the nutrient medium are carbohydrates such as glucose, xylose, galactose, sucrose, glycerin, starch, dextrin, and the like. Other sources which may be included are maltose, rhamnose, raffinose, arabinose, mannose, salicin, sodium succinate, and the like.

The preferred sources of nitrogen are meat extract, yeast extract, peptone, gluten meal, cotton-seed meal, soybean meal, cotton-seed flour, soybean flour, corn steep liquor, dried yeast, wheat germ, feather meal, peanut powder etc., as well as inorganic and organic nitrogen compounds such as ammonium salts (e.g. ammonium nitrate, ammonium sulfate, ammonium phosphate, etc.), urea, amino acid, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salt and the like. If necessary, especially when the culture medium foams seriously, a defoaming agent, such as liquid paraffin, fatty oil, plant oil, mineral oil or silicone may be added.

As the conditions for the production of the FR-900493 substance in massive amounts, submerged aerobic cultural conditions are preferred therefor. For the production in small amounts, a shaking or surface culture in a flask or bottle is employed. Furthermore, when the growth in carrier out in large tanks, it is preferable to use the vegetative form of the organism for inoculation in the production tanks in order to avoid growth lag in the process of production of the FR-900493 substance. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. The medium, in which the vegetative inoculum is produced, is substantially the same as or different from the medium utilized for the production of the FR-900493 substance.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°-35° C., for a period of about 20 hours to 150 hours, which may be varied according to fermentation conditions and scales.

Thus produced FR-900493 substance can be recovered from the culture medium by conventional means which are commonly used for the recovery of other known biologically active substances. The FR-900493 substance produced and found in the cultured filtrate and mycelium, and accordingly the FR-900493 substance can be isolated and purified from the filtrate and the mycelium, which is obtained by filtering or centrifuging the cultured broth, by a conventional method such as concentration under reduced pressure, lyophilization, extraction with a conventional solvent, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like.

The FR-900493 substance produced according to the aforementioned process possesses the following physical and chemical properties.

(1) Appearance:
White powder
(2) Nature:
Amphoteric
(3) Melting point:
157°-160° C. (dec.)
(4) Specific rotation
$[\alpha]_D^{25}: +27°$ (c 1.0, $H_2O$)
(5) Molecular formula:
$C_{20}H_{33}N_5O_{11}$
(6) Elemental analysis. Calcd for $C_{20}H_{33}N_5O_{11} \cdot 2H_2O$ C 43.23, H 6.71, N 12.61 (%) Found C 43.34, H 6.56, N 12.68 (%)
(7) Molecular weight:
SI-MS: m/z 520 ($M^+ + 1$)
(8) Solubility:
Soluble: Water
Insoluble: Methanol, Acetone, Ethyl acetate, Chloroform
(9) Color reaction:
Positive: each reaction with ninhydrin, iodine, cerium sulfate and potassium permanganate, Molish reaction⊕
Negative: each reaction with ferric chloride and Diacetyl agent
(10) Thin Layer Chromatography:
Stationary phase
Silica gel (Kieselgel 60 F-254 made by Merck)
Developing Solvent
n-butanol:ethanol:chloroform: 28% aqueous ammonia = 4:7:2:7 V/V
Rf Value
0.10
(11) UV:
$\lambda_{max}^{H_2O}$ 262 nm ($E_{1\ cm}^{1\%}$ 245) ($\epsilon$12,700)
$\lambda_{max}^{0.1N\ HCl}$ 260 nm ($E_{1\ cm}^{1\%}$ 240) ($\epsilon$12,450)
$\lambda_{max}^{0.1N\ NaOH}$ 262 nm ($E_{1\ cm}^{1\%}$ 190) ($\epsilon$9,850)
(12) IR (KBr):
νmax: 3650-2200 (br), 1670, 1620, 1570, 1555, 1540, 1500, 1495, 1390, 1350, 1340, 1270, 1240, 1170, 1100, 1050, 1000, 950, 920, 860, 820, 780 cm$^{-1}$,
the chart of which is shown in FIG. 1,
(13) $^1$H NMR ($D_2O$):
δppm: 1.70-2.00 (2H, m), 2.41 (3H, s), 2.44-2.68 (1H, m), 2.70-2.92 (1H, m), 3.00-3.31 (4H, m), 3.50 (1H, d, J=8 Hz), 4.05-4.34 (8H, m), 5.21 (1H, br s), 5.75 (1H, d, J=2 Hz), 5.82 (1H, d, J=8 Hz), 7.79 (1H, d, J=8 Hz), the chart of which is shown in FIG. 2,
(14) $^{13}$C NMR ($D_2O$):
δppm: 175.7, 171.3, 155.2, 141.9, 110.1, 102.4, 91.4, 83.7, 80.7, 78.5, 75.4, 74.2, 71.4, 71.3, 69.9, 52.3, 41.8, 39.0, 38.7, 25.0,
the chart of which is shown in FIG. 3.

BIOLOGICAL PROPERTIES OF THE FR-900493 SUBSTANCE

The FR-900493 substance possesses pharmacological activities such as antimicrobial activity or the like, and therefore is useful for the treatment and prevention of infectious diseases caused by pathogenic microorganisms, and the like.

As an example for showing such pharmacological activity, some pharmacological test data are illustrated in the following.

Test 1

Antimicrobial activities:

(a) Test Method

One loopful of an overnight culture ($10^8$ cells/ml) of each test bacteria in bouillon was streaked on ½ Mueller-Hinton agar containing the graded concentration of the FR-900493 substance and the minimal inbibitory concentration (MIC) was determined after incubation at 37° C. for 24 hours.

(b) Test Results

| Test Bacteria | | MIC ($\mu$g/ml) |
|---|---|---|
| Staphylococcus aureus | 209P JC-1 | 3.13 |
| | 1601-6 | 6.25 |
| Bacillus subtilis | ATCC-6633 | 3.13 |

Test 2

Protective efficacy in experimental infections in mice:

The in vivo activity of the FR-900493 substance against experimental infections due to Staphylococcus aureus 1601-47 was examined. One hour after the intraperitoneal injection of $3 \times 10^6$ cell of the test strain to each ddY mouse (male, 5 weeks age), the solution of the FR-900493 substance was administered subcutaneously. The mice were observed for 2 days.

| Staphyloccus aureus 1601-47 | | |
|---|---|---|
| Sample | Dose | Survival (%) |
| FR-900493 substance | 30 mg/kg | 100 |

Test 3

Acute toxicity:

The median lethal dose ($LD_{50}$) of the FR-900493 substance in mice (ddY, 4 weeks age, male) by intravenous administration was >500 mg/kg.

The pharmaceutical composition of this invention can be used in the form of a pharmaceutical preparation, for example, in solid, semisolid or liquid form, which contains the FR-900493 substance, as an active ingredient, in admixture with an organic or inorganic carrier or excipient suitable for external, enternal or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

For applying this composition to human, it is preferable to apply it by parenteral or enteral administration. While the dosage of therapeutically effective amount of the FR-900493 substance varies from and also depends upon the age and condition of each individual patient to be treated, a daily dose of about 0.01–1000 mg, preferably 0.1–500 mg and more preferably 0.5–100 mg, of the active ingredient is generally given for treating diseases, and an average single dose of about 0.5 mg, 1 mg, 5 mg, 10 mg, 50 mg, 100 mg, 250 mg and 500 mg is generally administered.

The following examples is given for the purpose of illustrating the present invention.

EXAMPLE 1

Fermentation

An aqueous seed medium (80 ml) containing 2% bouillon was poured into a 250 ml Erlenmeyer flask and sterilized at 125° C. for 30 minutes. A loopful of Bacillus cereus No. 2045 on mature slant culture was inoculated to the seed medium. The flask was shaken on a rotary shaker (220 rpm, 5.1 cm throw) at 30° C. for 10 hours. An aqueous production medium (80 ml) containing 2% polypeptone, 2% corn steep liquor, 0.5% sodium chloride (pH 7.5) was poured into each of two hundred and thirty 250 ml flasks and sterilized at 120° C. for 30 minutes. The resultant seed culture broth (0.8 ml) was inoculated to each of the production medium and cultured on a rotary shaker (220 rpm, 7.5 cm throw) at 30° C. for 40 hours.

Progress of fermentation was monitored by standard disk-agar diffusion assay of supernatant fluid from a centrifuged broth sample (2,000 rpm, 10 minutes). Pseudomonas aeruginosa IV, supersensitive mutant to nalidixic acid derivatives, was used as a test organism for the bioassay.

Isolation and Purification (a) The cultured broth (17 l) was filtrated with the aid of filter aid (Radiorite 600 (0.5 kg): Trademark, made by Showa Chemical Industry). The filtrate (16 l, pH 9.5) was adjusted to pH 6.0 with 1N hydrochloric acid and passed through a column of activated carbon (made by Wako Pure Chemical, 1 l). The column was washed with water (2 l) and 60% aqueous acetone (2 l), and then eluted with 60% aqueous acetone containing 0.28% ammonia (4 l). The eluate was concentrated to 1.5 l aqueous solution under reduced pressure. The concentrate was chromatographed on column of "Dowex 1×2" (OH$^-$ form) (Trademark, made by Dow Chemical Co., Ltd.,) (200 ml). The column was washed with water (500 ml) and 0.1M sodium chloride (500 ml), and then eluted with 0.3M sodium chloride (1.2 l). The eluate was applied on a column of activated carbon (200 ml). The column was washed with water (600 ml) and 60% aqueous acetone (600 ml), and then eluted with 60% aqueous acetone containing 0.28% ammonia (600 ml). The eluate was concentrated to 100 ml aqueous solution under reduced pressure. The concentrate was chromatographed on a column of "CM-Sephadex C-25" ($NH_4^+$ form) (Trademark, made by Pharmacia Fine Chemical Co., Ltd.) (20 ml). The column was washed with water (40 ml) and eluted with 0.28% aqueous ammonia. The eluate was concentrated under reduced pressure. The residue was chromatographed on a column of silica gel (Kieselgel 60, made by E. Merck) (80 ml) with a solution of n-butanol-ethanol-chloroform-28% aqueous ammonia (4:7:2:7). The active fractions were combined and concentrated to 10 ml aqueous solution under reduced pressure. The resultant solution was chromatographed on a column of "CM-Shephadex C-25" (NH$_4^+$) (10 ml) to remove the silica gel. The column was washed with water (40 ml) and eluted with 0.28% aqueous ammonia (20 ml). The eluate was concentrated under reduced pressure and the resultant aqueous solution was freeze-dried to give a white powder of FR-900493 substance (161 mg).

(b) The filtrate (17 l, pH 10.0) was adjusted to pH 6.0 and passed through a column of activated carbon (1 l). The column was washed with water (2 l) and 60% aqueous acetone (2 l), and then eluted with 60% aqueous acetone containing 0.28% ammonia (5 l). The eluate was concentrated to 2 l aqueous solution under reduced pressure. The concentrate was chromatographed on a column of "CM-Sephadex C-25" (NH$_4^+$ form) (300 ml). The column was washed with water (600 ml) and eluted with 0.28% aqueous ammonia (300 ml). The eluate was concentrated under reduced pressure. The residue was chromatographed on a column of silica gel (200 ml). The object substance was eluted with a solution of n-butanol-ethanol-chloroform-28% aqueous ammonia (4:7:2:7). The eluate was concentrated under reduced pressure. The concentrate (100 ml) was chromatographed on a column of "CM-Sephadex C-25" (NH$_4^+$ form) (30 ml) to remove the silica gel. The column was washed with water (100 ml) and eluted with 0.1% aqueous ammonia (100 ml). The eluate was concentrated under reduced pressure and the resultant aqueous solution was freeze-dried to give a white powder of FR-900493 substance (479 mg).

Figure 1:
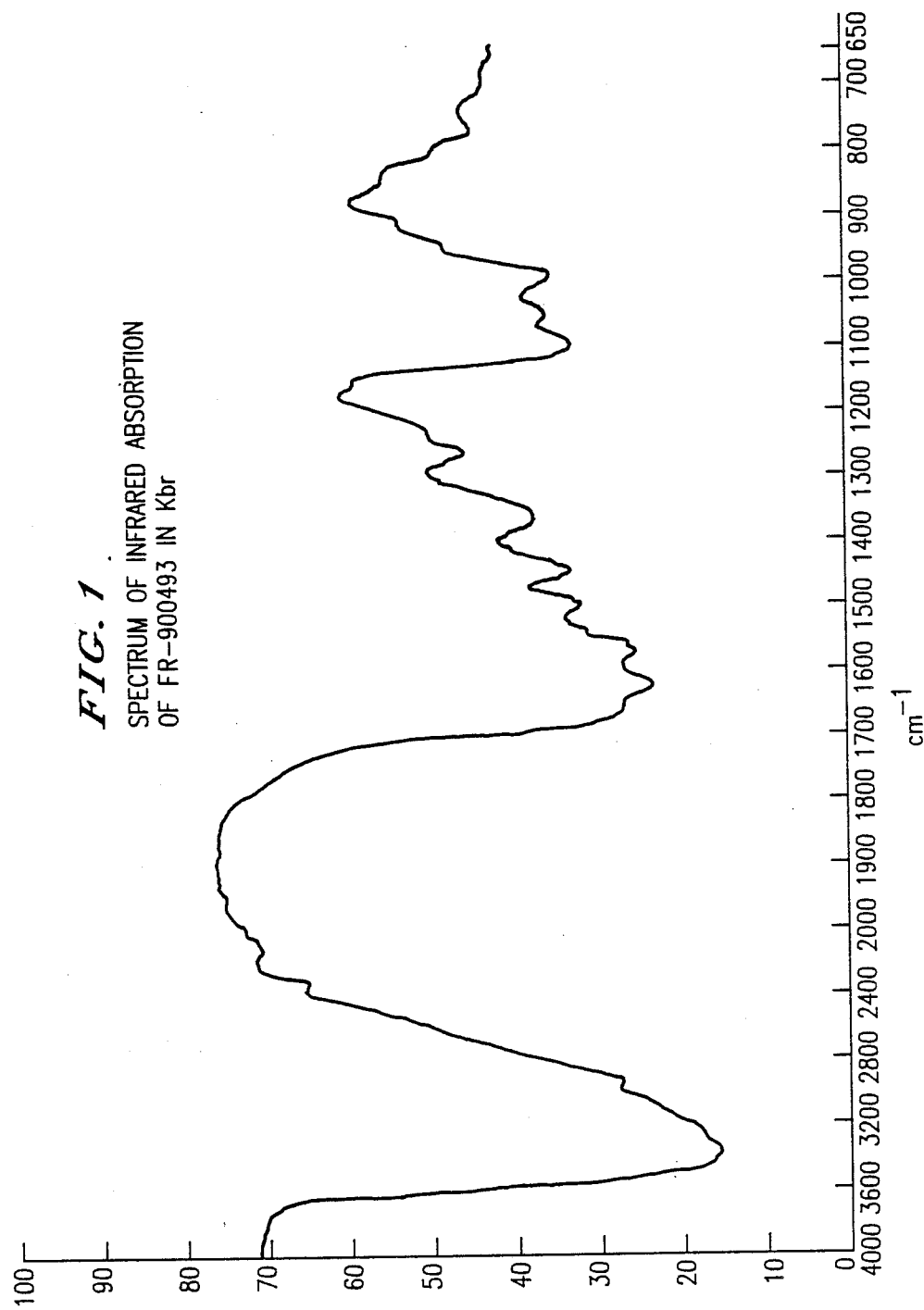
FIG. 1 is infrared absorption spectrum of FR-900493 substance in KBr.
Figure 2:
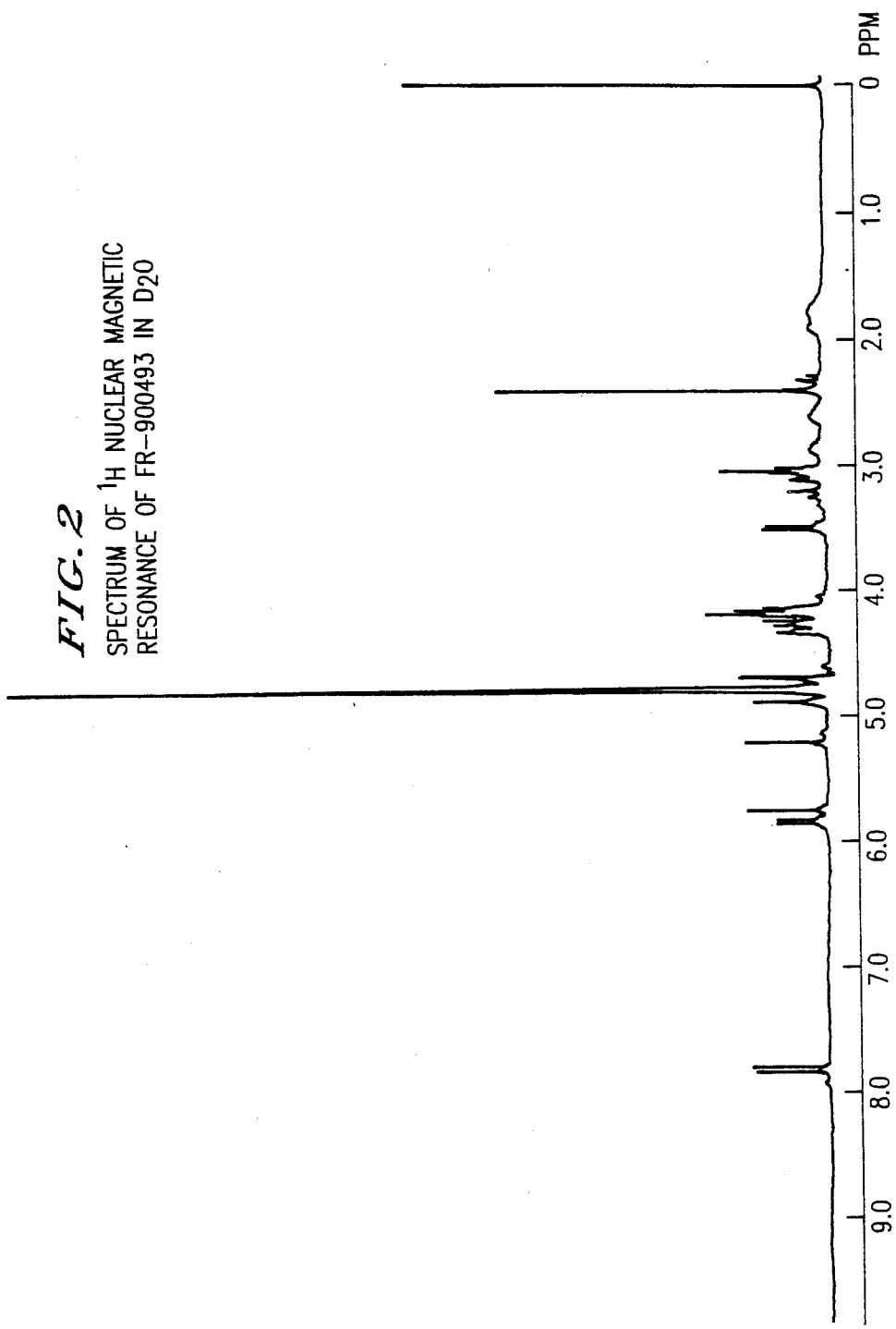
FIG. 2 is $^1$H nuclear magnetic resonance spectrum of FR-900493 substance in D$_2$O.
Figure 3:
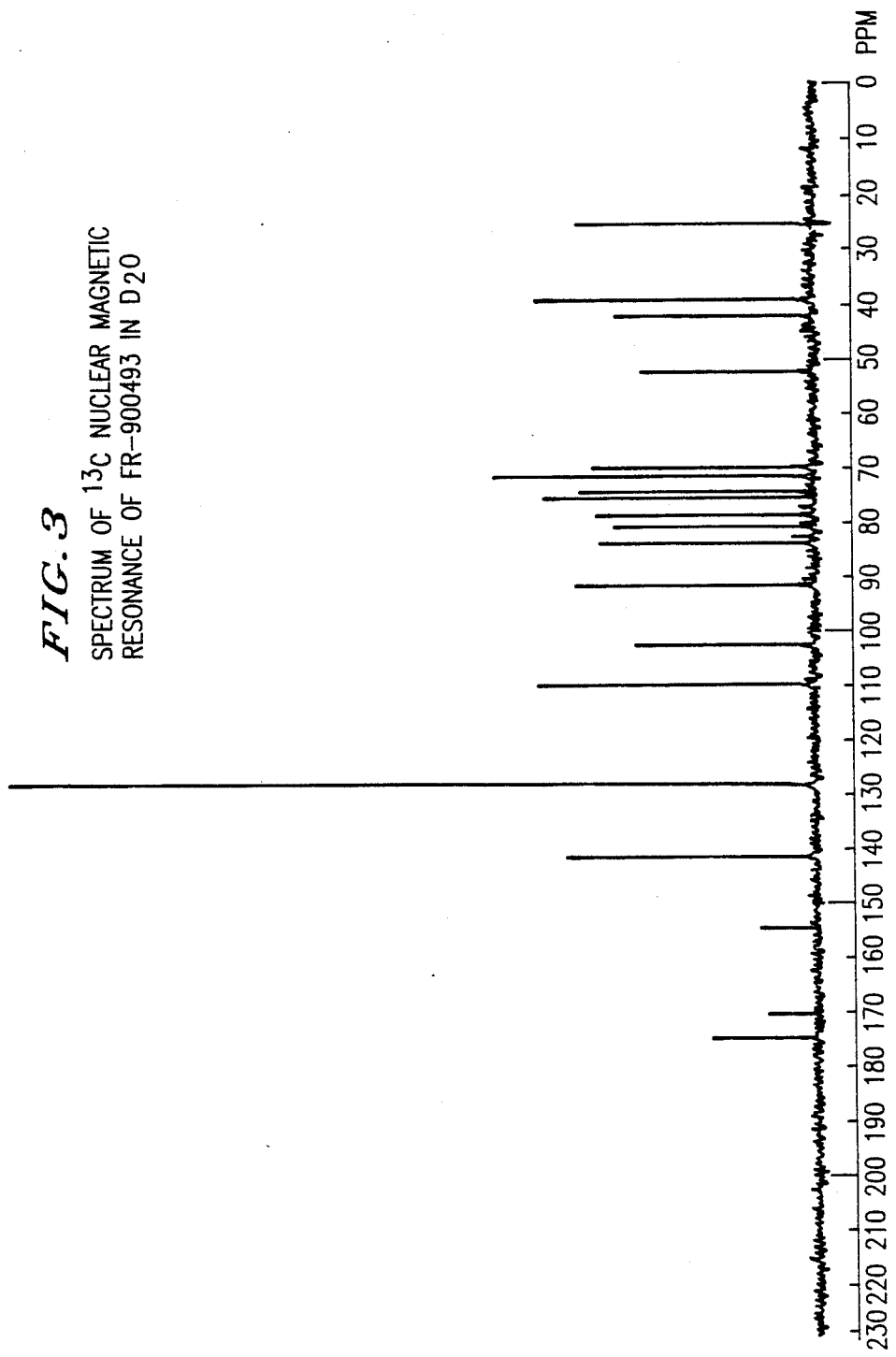
FIG. 3 is $^{13}$C nuclear magnetic resonance spectrum of FR-900493 substance in D$_2$O.

What we claim is:

1. A FR-900493 substance having the following physical and chemical properties.
   (1) Apperance:
      White powder
   (2) Nature:
      Amphoteric
   (3) Melting point:
      157°–160° C. (dec.)
   (4) Specific rotation:
      $[\alpha]_D^{25}$: +27° (c 1.0, H$_2$O)
   (5) Molecular formula:
      C$_{20}$H$_{33}$N$_5$O$_{11}$
   (6) Elemental analysis:
      Calcd. for C$_{20}$H$_{33}$N$_5$O$_{11}$.2H$_2$O: C 43.23, H 6.71, N 12.61 (%) Found: C 43.34, H 6.56, N 12.68 (%)
   (7) Molecular weight
      SI-MS: m/z 520 (M$^+$ + 1)
   (8) Solubility:
      Soluble: Water
      Insoluble Methanol, Acetone, Ethyl acetate, Chloroform
   (9) Color reaction:
      Positive: each reaction with ninhydrin, iodine, cerium sulfate and potassium permanganate, Molish reaction$\oplus$
      Negative: each reaction with ferric chloride and Diacetyl agent
   (10) Thin Layer Chromatography:
      Stationary phase
         Silica gel (Kieselgel 60 F-254 made by Merck)
      Developing Solvent
         n-butanol:ethanol:chloroform:28% aqueous ammonia=4:7:2:7 V/V
      Rf Value
         0.10
   (11) UV:
      $\lambda_{max}^{H2O}$ 262 nm (E$_1$ $_{cm}^{1\%}$ 245) ($\epsilon$12,700)
      $\lambda$0.1$_{max}^{0.1NHCL}$ 260 nm (E$_1$ $_{cm}^{1\%}$ 240) 9$\epsilon$12,450)
      $\lambda_{max}^{0.1NNaOH}$ 262 nm (E$_1$ $_{cm}^{1\%}$ 190) ($\epsilon$9,850)
   (12) IR (KBr):
      $\nu$max: 3650–2200 (br), 1670, 1620, 1570, 1555, 1540, 1500, 1495, 1390, 1350, 1340, 1270, 1240, 1170, 1100, 1050, 1000, 950, 920, 860, 820 780 cm$^{-1}$
   (13) $^1$H NMR (D$_2$O):
      $\delta$ppm: 1.70–2.00 (2H, m), 2.41 (3H, s), 2.44–2.68 (1H, m), 2.70–2.92 (1H, m), 3.00–3.31 (4H, m), 3.50 (1H, d, J=8 Hz), 4.05–4.34 (8H, m), 5.21 (1H, br s), 5.75 (1H, d, J=2 Hz), 5.82 (1H, d, J=8 Hz), 7.79 (1H, d, J=8 Hz)
   (14) $^{13}$C NMR (D$_2$O):
      $\delta$ppm: 175.7, 171.3, 155.2, 141.9, 110.1, 102.4, 91.4, 83.7, 80.7, 78.5, 75.4, 74.2, 71.4, 71.3, 69.9, 52.3, 41.8, 39.0, 38.7, 25.0

2. A process for preparing FR-900493 substance of claim 1, which comprises culturing a strain belonging to the genus Bacillus, which is capable of producing said FR-900493 substance, in a nutrient medium until a sufficient amount of said FR-900493 substance is imparted to said medium and recovering said FR-900493 substance.

3. The process of claim 2, wherein said strain belonging to the genus Bacillus is Bacillus cereus No. 2045 (FERM-1791).

4. A pharmaceutical composition, comprising a pharmaceutically effective amount of FR-900493 substance of claim 1, as an active ingredient, in association with a pharmaceutically acceptable, substantially non-toxic carrier or excipient.

5. A method for treating or preventing a microbial infectious disease which comprises administering an antimicrobially effective amount of the FR-900493 substance to a human or animal in need thereof.

6. A biologically pure culture of the microorganism Bacillus cereus No. 2045 (FERM BP-1791).

* * * * *